United States Patent [19]

Timmermans

[11] Patent Number: 4,581,025
[45] Date of Patent: Apr. 8, 1986

[54] SHEATH

[75] Inventor: Hans A. Timmermans, Bloomington, Ind.

[73] Assignee: Cook Incorporated, Bloomington, Ind.

[21] Appl. No.: 551,416

[22] Filed: Nov. 14, 1983

[51] Int. Cl.$^4$ ............................................ A61M 25/00
[52] U.S. Cl. ................................. 604/264; 604/160; 604/164
[58] Field of Search ............... 604/164, 166, 160, 264, 604/280; 128/784

[56] References Cited

U.S. PATENT DOCUMENTS 4,243,050  1/1981  Littleford ........................... 128/784
4,306,562 12/1981  Osborne ........................... 604/164 X Primary Examiner—Stephen C. Pellegrino
Attorney, Agent, or Firm—Woodard, Weikart, Emhardt & Naughton

[57] ABSTRACT

A sheath comprising a tubular structure formed of a flexible material which is compatible for insertion within the body and having proximal and distal ends. In one embodiment, the tubular structure includes one slit having an open and a closed end. The tubular structure is further comprised of a tab defined by the slit whereby, when the tab is pulled apart from any object extending through the lumen of the tubular structure, the tubular structure tears longitudinally removing the tubular structure from the object. In another embodiment, the tubular structure is cuffed between the closed end of the slit and the distal end of the tubular structure, the cuff defining the proximal end of the tubular structure. The cuff prevents the slit from tearing prematurely and further provides a blunt, smooth open end at the proximal end that permits closure thereof by thumb pressure only in order to temporarily block blood flow or air aspiration during use.

5 Claims, 7 Drawing Figures s# SHEATH

BACKGROUND OF THE INVENTION

The present invention relates generally to a sheath used to facilitate percutaneous insertion of devices, such as catheters, into the body and, more specifically, to a sheath which can be torn off after insertion.

The use of catheters to inject, sample, drain, biopsy and implant various instruments in the body has developed into a highly sophisticated area of medical practice. Introduction of catheters into the vascular system without surgical cut down has been practiced for many years under what is termed the Seldinger technique. This technique involves the percutaneous insertion of a catheter through the use of a hollow needle and a wire guide. One modification of this technique, known as the Desilets-Hoffman technique, involves the use of an introducer sheath to permit the percutaneous insertion of a catheter or other instrument not having an open lumen or tapered tip.

In certain situations, such as for example, the transvenous insertion of pacemaker leads into the body, it is not possible to remove the introducer sheath from the inserted instrument unless the sheath is first split longitudinally. As a result, several devices have been developed which disclose a means for splitting the sheath longitudinally after insertion into the body. The most satisfactory one of these devices, and that upon which the present invention is a direct improvement, is disclosed in U.S. Pat. No. 4,306,562 to Osborne. This patent discloses a tear apart cannula made from a flexible material exhibiting the property of longitudinal molecular orientation. The cannula is provided with a pair of longitudinal slits defining tabs at the proximal end of the cannula. While the slits run only a portion of the total length of the cannula, due to the longitudinal molecular orientation construction, the cannula is capable of easily tearing apart so as to permit its removal from any object received therein.

While the Osborne cannula stands as a distinct improvement over other cannulas designed for similar use, there are nevertheless some disadvantages occasioned by its use. One such disadvantage is that the Osborne cannula requires that both hands of the user be employed to manipulate the cannula so as to tear it apart. Further, the Osborne cannula must inherently be split into two for removal, thus creating two pieces of material for disposal. Another disadvantage involves the manner in which the user can temporarily block blood flow or air aspiration when there are no dilators or catheters in the lumen of the introducer cannula. The standard accepted practice used with more conventional introducer cannulas permits the user to block blood flow or air aspiration by placing his thumb over the proximal open end of the cannula and exerting pressure. The Osborne cannula requires the user to squeeze or pinch off the lumen of the sheath at the proximal end. This procedure has encountered some resistance since some physicians fear this damages the cannula and compromises the lumen size. Also in some situations it is desired to use a needle stylet in the sheath so that the sheath can be inserted and advanced into the tissue. Since there is no regular bearing surface at the proximal end of the Osborne cannula, it has been observed that the cannula slits will prematurely tear while it is being inserted and advanced into the tissue with a needle therein. Thus the distance between the needle point and the distal end of the cannula cannot be established and maintained during use.

SUMMARY OF THE INVENTION

One embodiment of this invention might involve a sheath including a tubular structure formed of a flexible material which is compatible for insertion within the body and having proximal and distal ends. The tubular structure is further characterized by having one or more slits, each having an open and a closed end. At least one tab is defined by the one or more slits whereby, when the tab is pulled apart from any object extending through the lumen of the tubular structure, the tubular structure tears longitudinally peeling away the tubular structure from the object. Additionally, the tubular structure is provided with means for preventing the tubular structure from tearing prematurely along the one or more slits.

It is an object of the present invention to provide an improved sheath for use in facilitating percutaneous insertion of devices, such as catheters, into the body.

It is a further object of the present invention to provide an improved sheath which permits the user to temporarily block blood flow or air aspiration during use when there are no dilators or catheters in the sheath lumen without having to pinch off or otherwise restrict the lumen size.

It is a yet further object of the present invention to provide an improved sheath of the type having one or more longitudinal slits which is also provided with means for preventing the slit or slits from tearing prematurely during use.

Another object of the present invention is to provide an improved sheath which provides a definite bearing surface at the proximal end against which the fitting or hub of a needle stylet or other instrument can bear during use.

An additional object of the present invention is to provide an improved sheath which may be removed by manipulating it in one hand, thereby leaving the other hand free to grasp other elements of the catheter assembly.

Yet another object of the present invention is to provide an improved disposable peel away sheath which, after removal, presents only one piece for disposal.

Related objects and advantages of the present invention will be made more apparent by reference to the following figures and detailed description.

DESCRIPTION OF THE PREFERRED EMBODIMENT

Figure 1:
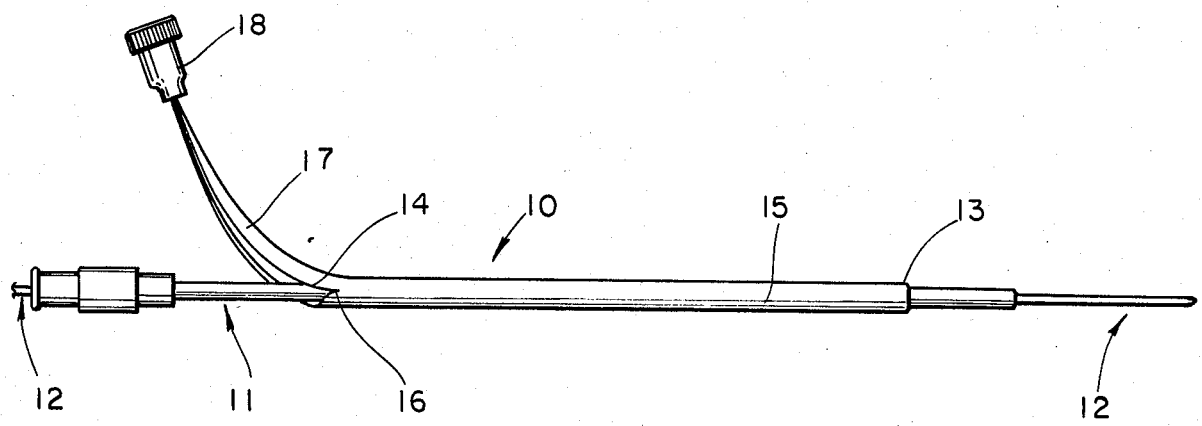
FIG. 1 is a side elevation view of the preferred embodiment of the sheath in combination with a dilator and a wire guide.
Figure 2:
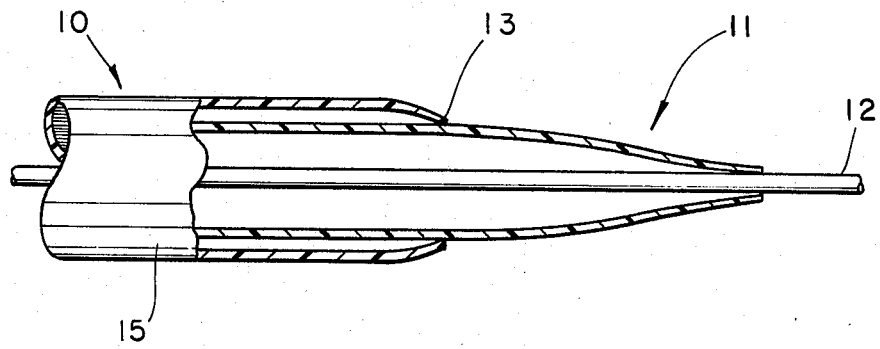
FIG. 2 is an enlarged fragmentary view of the structure of FIG. 1, with portions thereof broken away to show internal features.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
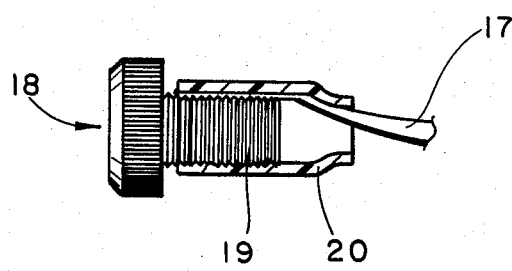
FIG. 3 is an enlarged fragmentary view, partially in section, of the sheath of FIG. 1 showing details of construction of the tab.

Referring now to the drawings in detail, there is shown in FIG. 1 a preferred embodiment of the sheath generally designated at 10 in combination with a dilator 11 and a wire guide 12. Sheath 10 is disposed over dilator 11 which is in turn disposed over wire guide 12. Dilator 11 and wire guide 12 are of conventional design and thus a detailed description of their construction is not necessary for those of ordinary skill in the art. It is sufficient to note that dilator 11 is correspondingly sized with sheath 10 and possesses a slight taper so as to enlarge the puncture site sufficiently to accommodate the introduction of sheath 10 therein. The distal portion of sheath 10 is provided with a rounded or tapered tip 13 to ensure a desirably snug fit between dilator 11 and sheath 10 and facilitate smooth introduction of sheath 10 within the body. Sheath 10 includes a generally tubular portion 15 which defines a slit 14 beginning at the proximal end of tubular portion 15 and continuing longitudinally therefrom along a portion of sheath 10 to closed end 16. The longitudinal slit 14 defines a tab 17 integral with tubular portion 15, the proximal end of tab 17 being attached to a knob 18 between screw portion 19 and socket portion 20 thereof (FIG. 3). Knob 18 serves to facilitate gripping and pulling tab 17 as sheath 10 is peeled apart.

The sheath of the preferred embodiments is made of Teflon (Teflon is the Dupont trademark for polytetrafluoroethylene) and which also is virgin material, for body compatibility purposes. The sheath is longitudinally molecularly oriented according to the method disclosed in U.S. Pat. No. 4,306,562 to Osborne. This ensures that the sheath will tear apart in a desired longitudinal fashion so as to separate the sheath from any instrument received therein. It should nevertheless be understood that the longitudinal molecular orientation of the sheath and the method for attaining same is not necessary to the present invention. In other words, the invention can be practiced and is practiced in the preferred embodiment using such orientation. Alternatively, longitudinal tearing can be accomplished by preweakening the sheath by a groove or the like so that the sheath tears along such groove or grooves.

In the manufacturing of the cannula, the Teflon tubing is cut off radially to define one end of the cannula and slit at that one end with a cutting instrument to form slit 14. This slitting operation creates the tab 17 which is used to pull apart the sheath, the closed end 16 of slit 14 defining the location of the beginning of the peeling when the tab 17 is pulled.

Figure 4:
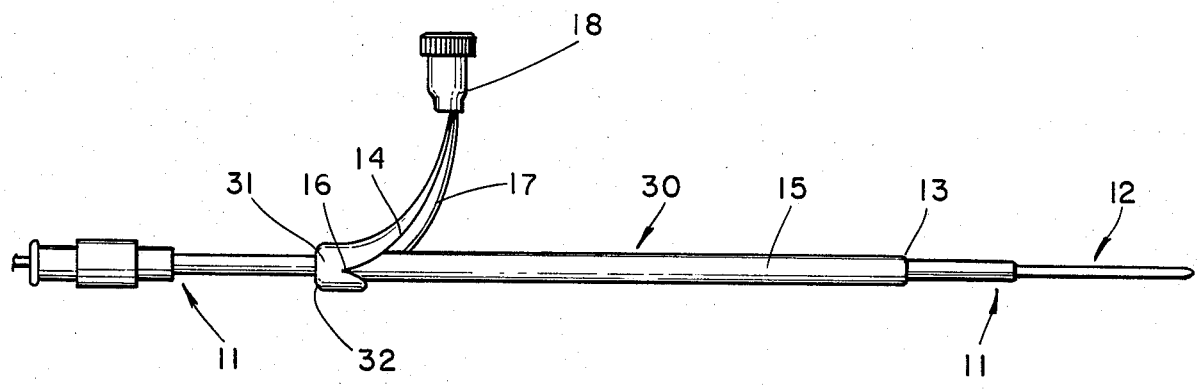
FIG. 4 is a side elevation view of a first alternative preferred embodiment of the sheath in combination with a dilator and a wire guide.

FIG. 4 shows a first alternative preferred embodiment of the sheath generally designated at 30 disposed over dilator 11 and wire guide 12. It should be noted that where elements in this and the following embodiments correspond to those of the previous embodiment, similar numerals are used to designate them. In this embodiment, otherwise similar to the embodiment of FIG. 1, the tubular portion of the sheath is folded over slightly ahead of the closed end of the slit so as to define a cuff 31. At least several advantages are afforded by this novel arrangement. The presence of cuff 31 provides a blunt, smooth open end at the proximal end 32 of the sheath lumen which permits temporary blocking of blood flow or air aspiration therethrough during use when there are no instruments within the sheath lumen. This is simply accomplished by placing a thumb over the end 32 in a manner generally similar to that depicted for the embodiment shown in FIG. 6. Another advantage of cuff 31, illustrated in FIG. 7, is that it provides a bearing surface against which a needle stylet hub or fitting can bear during insertion into the body. Not only does this facilitate needle stylet insertion, it also provides a definite stop which limits the distance the stylet can be inserted in the sheath and thereby establishes and maintains the distance between the point of the needle stylet and the distal end of the sheath during use. It should be particularly noted that the presence of cuff 31 does not prevent or unduly restrict the tearing apart of the sheath when the tabs are pulled apart, but does serve to prevent premature tearing of the sheath when instruments, such as dilator 11, are positioned inside the sheath lumen.

Figure 5:
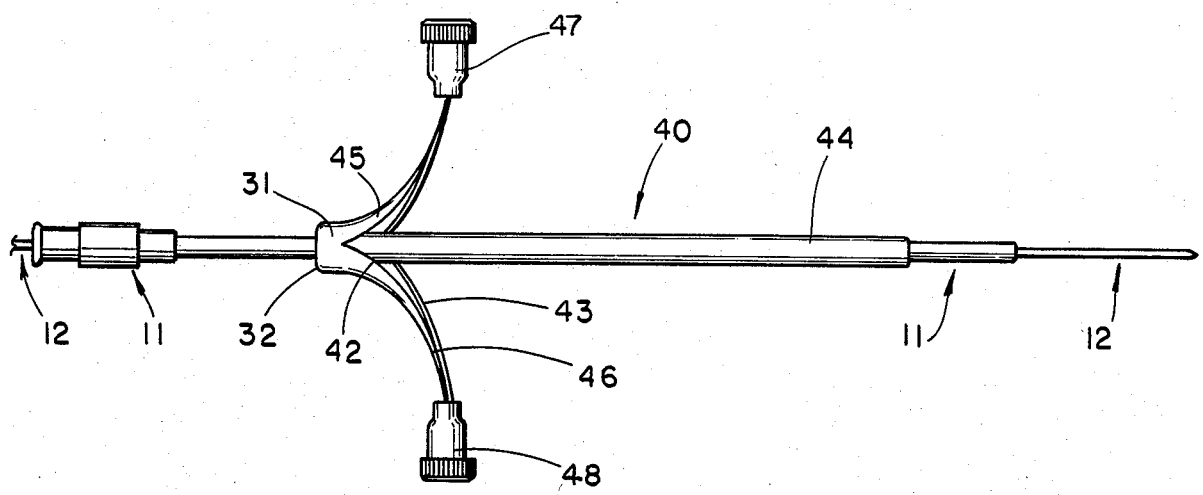
FIG. 5 is a side elevation view of a second alternative preferred embodiment of the sheath in combination with a dilator and a wire guide.

FIG. 5 depicts a second alternative preferred embodiment of the sheath generally designated at 40 disposed over dilator 11 and wire guide 12. In this embodiment, otherwise similar to the embodiment depicted in FIG. 4, the cuff 31 is employed with a sheath having a pair of slits 42 and 43 oppositely located radially on the tubular portion 44 and defining a pair of tabs 45 and 46 fitted with knobs 47 and 48, respectively.

Figure 6:
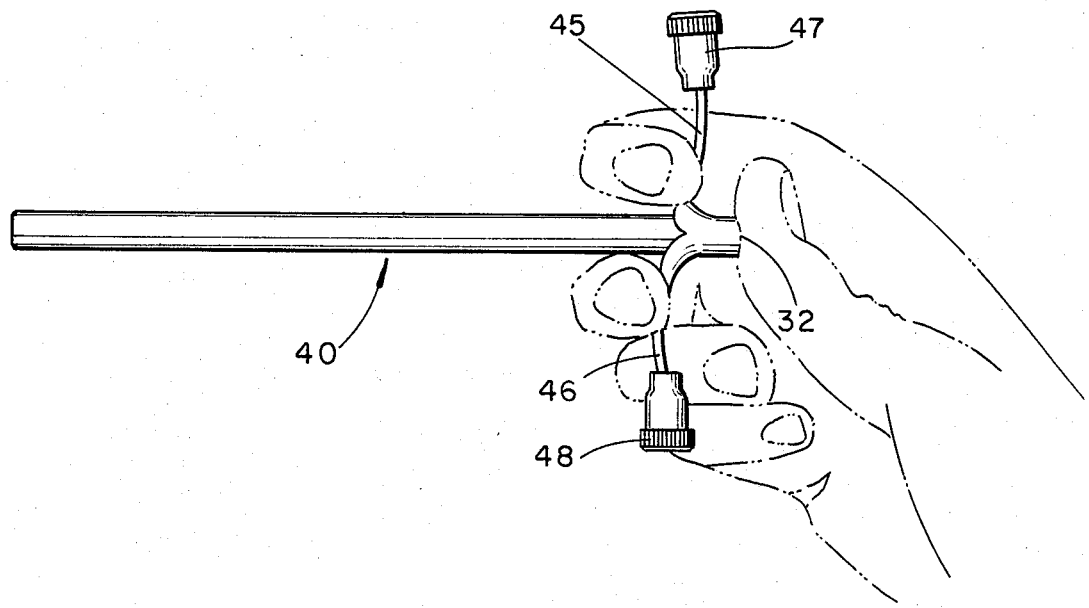
FIG. 6 illustrates the manner in which the sheath of FIG. 5 is manipulated in order to temporarily block blood flow or air aspiration during use.
Figure 7:
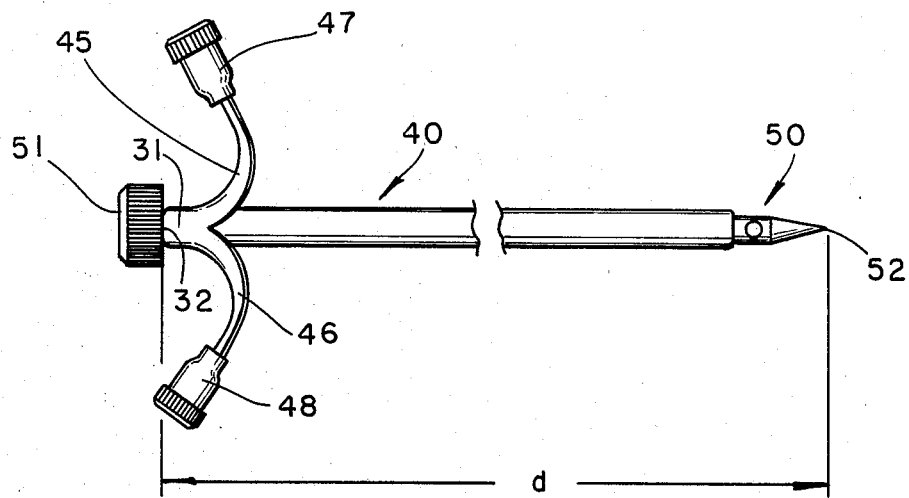
FIG. 7 illustrates a needle stylet fully inserted within the sheath of FIG. 5.

FIG. 6 shows the manner in which the sheath 40 is gripped in order to temporarily block blood flow or air aspiration through the sheath lumen. Thus, the sheath lumen is blocked by placing the thumb over the cuffed open end 32 of the sheath lumen and exerting pressure while the first and second fingers are curled around and pressed against the tabs 45 and 46. FIG. 7 shows sheath 40 disposed over a needle stylet 50 fully inserted within the sheath lumen. The fitting 51 of stylet 50 bears directly against cuff 31 establishing a fixed distance d between the stylet point 52 and the distal end 32 of the sheath lumen. It may be perceived that cuff 31 prevents stylet 50 from tearing slits 42 and 43 as it is fully inserted within the sheath.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A sheath having:
   a tubular structure formed of a flexible material which is compatible for insertion within a body wherein the improvement comprises having proximal and distal ends, said tubular structure having one or more slits, each said one or more slits having an open and a closed end;

a tab defined by said one or more slits on said proximal end of said tubular structure whereby, when said tab is pulled apart from any object extending through the lumen of said tubular structure, said tubular structure tears longitudinally along its length from said closed end of said one or more slits, removing said tubular structure from said object; and a cuff between said closed end of said one or more slits and said distal end of said tubular structure, said cuff defining said proximal end of said tubular structure and providing a blunt, smooth open end at said proximal end of said tubular structure that permits closure thereof by covering said open proximal end with the thumb.

2. The sheath of claim 1 wherein said flexible material having the property of molecular orientation whereby a tear in said material runs readily only in a longitudinal direction along the length of said tubular structure.

3. The sheath of claim 2 wherein said tubular structure is continuously smooth along its inner and outer surface.

4. The sheath of claim 3 wherein said tubular structure includes exactly one slit.

5. The sheath of claim 3 wherein said tubular structure includes a pair of slits.

* * * * *